United States Patent [19]

Gasser et al.

[11] Patent Number: 5,024,711
[45] Date of Patent: Jun. 18, 1991

[54] METHOD FOR PREPARING A SUBSTRATE SURFACE FOR BONDING WITH A SYNTHETIC RESIN BY APPLYING A LAYER BY SAND BLASTING

[75] Inventors: Oswald Gasser; Rainer Guggenberger, both of Seefeld; Bernd Burger, Alling, all of Fed. Rep. of Germany

[73] Assignee: Thera, Starnberg, Fed. Rep. of Germany

[21] Appl. No.: 301,019

[22] Filed: Jan. 24, 1989

[30] Foreign Application Priority Data

Jan. 25, 1988 [DE] Fed. Rep. of Germany ....... 3802042

[51] Int. Cl.$^5$ ............................................... B24C 1/00
[52] U.S. Cl. ......................................... 156/153; 51/319; 51/320; 427/203; 427/204; 427/2; 433/222.1
[58] Field of Search ................. 51/319, 320, 307–309; 156/153; 427/2, 290, 203, 204, 205, 201, 289; 433/222.1

[56] References Cited

U.S. PATENT DOCUMENTS

| | | | |
|---|---|---|---|
| 3,541,017 | 11/1970 | Muhler | 51/308 X |
| 3,647,381 | 3/1972 | Reiter | 52/308 |
| 4,364,731 | 12/1982 | Norling et al. | 433/222.1 X |
| 4,478,579 | 10/1984 | Fischer et al. | 433/222.1 |
| 4,544,377 | 10/1985 | Schwen | 51/306 X |
| 4,600,390 | 7/1986 | Göbel et al. | 427/2 X |

OTHER PUBLICATIONS

Ingulli, Charles N., "Abrasive Jet Machining", *The Tool and Manufacturing Engineer*, Nov. 1967, pp. 28–33.

*Primary Examiner*—John J. Gallagher
*Assistant Examiner*—Jeff H. Aftergut
*Attorney, Agent, or Firm*—Birch, Stewart, Kolasch & Birch

[57] ABSTRACT

The present invention relates to a method for preparing a surface for bonding with a synthetic resin. In the method, a layer is applied onto a substrate surface by sand blasting with a composition comprising (A) 0.01 to 90% by weight of an optionally silanized material having a particle size less than 5 μm and having a hardness greater than that of the substrate surface, and/or (B) 20 to 100% by weight of a silanized siliceous material having an average particle size of 2 to 200 μm, and (C) the remainder of the sand blasting composition having an average particle size greater than 5 μm, and optionally the layer is thereafter silanized. The invention is further directed to the above-mentioned composition.

23 Claims, 1 Drawing Sheet

METHOD FOR PREPARING A SUBSTRATE SURFACE FOR BONDING WITH A SYNTHETIC RESIN BY APPLYING A LAYER BY SAND BLASTING

FIELD OF THE INVENTION

The present invention relates to a method for preparing a substrate surface for bonding the substrate surface to a synthetic resin (e.g., with a synthetic resin-containing adhesive). The invention is further directed to a sand blasting composition used in the above-mentioned method.

BACKGROUND OF THE INVENTION

Adhesive bonds between substrate surfaces (e.g, wood, glass, metals, ceramics or synthetic resins) by means of synthetic resin-containing adhesives, or coatings of substrates with synthetic resins, should be durable in widely varying weather conditions. In the ideal case, the adhesive strength of the substrate-to-synthetic resin bond under all sorts of stress, such as mechanical or thermal deformation, should be stronger in all instances than the internal strength of the synthetic resin (cohesive strength).

When mounting a synthetic resin-covered crown facing on a metallic denture, it is particularly important to durably bond the synthetic resin to the metal without leaving any gaps in-between the resin and the metal. Deficient bonding results in a premature separation of the facing and in the formation of marginal gaps. Deficient bonding also possibly results in the discoloration of the margin as a result of oxidation of the metal skeleton. Moreover, deficient bonding results in a mechanical irritation of tissue along the gap between the facing and the metallic structure.

Inside the mouth a metal/synthetic resin bond or a ceramic synthetic resin bond is subject to special stress. First, these bondings are subject to physico-mechanical stress which occurs during chewing. Second, these bondings are subject to chemical-biological stress under the influence of saliva, food and pharmaceuticals. Moreover, the bond is subject to additional stress caused by temperature variations occurring in the mouth.

Hitherto, the solutions known in the art either produce bonds that are not sufficiently durable, or they require high apparative investment not normally acceptable in dental laboratories. In addition, these methods require the perfecting and mastering of the procedural steps thereof in order to obtain optimum bonds.

Accordingly, German Offenlegungsschrift 32 11 123 discloses a method for applying a crown facing onto a metallic denture, wherein the metallic crown body is roughened by sand blasting, then dipped several times into a silane-containing ultrasonic bath, and thereafter dried. Afterwards, the facing material is operation has several disadvantages. For instance, only silicon-containing non-precious metal alloys can be employed, and the adhesion which is achieved does not withstand long-term exposure to stress in the mouth.

U.S. Pat. No. 4,364,731 describes the preparation of a coupling layer of inorganic oxides (e.g., silica) which are applied onto the metallic surface by a so-called sputtering apparatus. The oxide layer which is obtained is silanized and thereafter the facing material is applied in a manner known per se. The sputtering process has the effect that the metallic surface to be coated is subject to very high temperatures. Moreover, the method can only be realized with enormous apparative investments in dental laboratories.

A further development of the technique described in the above mentioned U.S. patent is proposed in European patent publication 0 151 233. The European publication discloses that the silica-containing coupling layer is produced with a flame-hydrolysis burner. This bonding layer is silanized, and thereafter the synthetic resin facing material is applied in a manner known per se. In the method disclosed in the European publication, the work is also subjected to relatively high temperatures. Good adhesion is only achieved if all of the apparative parameters are strictly observed. However, the desired results can only be realized with a very high apparative investment.

Furthermore, German Offenlegungsschrift 36 42 290 describes a method for improving the adhesion of synthetic materials to metals, wherein a silica layer is applied onto the metallic surface by coating the metallic surface with silica sols or fine dispersions of ultrafine particulate silicic acid. The thus obtained layers are baked at temperatures of 100° to 800° C. However, in this method, the work is also subjected to high temperatures. Moreover, the adhesive strength which is attained is not sufficient for a durable restoration in the mouth when using the precious metals frequently used in dentistry. Conventional sand blasting with silica (E. Combe, "Zahnarztliche Werkstoffe", Carl Hanser Verlag Munchen-Wien, page 299, 1984; German Offenlegungsschrift 35 31 892 and "Metalloberflache", Vol. 37, page 335, 1983), or conventional sand blasting with alumina (Derwent Abstr., 84-228034/37—average particle size of 20 to 60 $\mu$m, and U.S. Pat. No. 4,504,228—particle size of about 150 $\mu$m), or surface treatment by centrifugal jet machines using steel grit (A.W. Mallory, Industrie-Lackier-Betrieb, page 223, 1985) only results in a cleaning and roughening of the metallic surface. Although particles may occasionally be catapulted onto the surface (K.-A. van Oeteren, "Korrosionsschutz durch Anstrichstoffe", Vol. 1, page 328, 1980), none of these techniques produce a coupling layer.

SUMMARY OF THE INVENTION

In view of the above-mentioned drawbacks of the prior art, it is an object of the present invention to prepare a substrate surface by applying a layer on the surface so that it is possible to achieve a durable bond between a synthetic resin and a substrate surface. The method is easily performed and does not require an extensive apparative investment. In addition, the work need not be exposed to extreme temperatures. Moreover, the method results in a substrate/synthetic resin bond that is stable towards varying physical, thermal, and hydrolytic stress.

According to the invention, the problems of the prior art are solved by a method for preparing a substrate surface for bonding with a synthetic resin, which comprises applying a layer onto the substrate surface by sand blasting with a composition which, on the basis of the weight of the entire sand blasting composition, comprises:

(A) 0.01 to 90% by weight of an optionally silanized material having a particle size less than 5 $\mu$m and having a hardness exceeding that of the substrate surface, and/or (B) 20 to 100% by weight of a silanized siliceous material having an average particle size of 2 to 200 μm, and (C) the remainder of the sand blasting composition having an average particle size greater than 5 μm, and thereafter optionally silanizing the thus obtained coupling layer.

The invention is further directed to a composition comprising components (A) and/or (B) and (C) as described above.

DETAILED DESCRIPTION OF THE INVENTION

Figure 1:
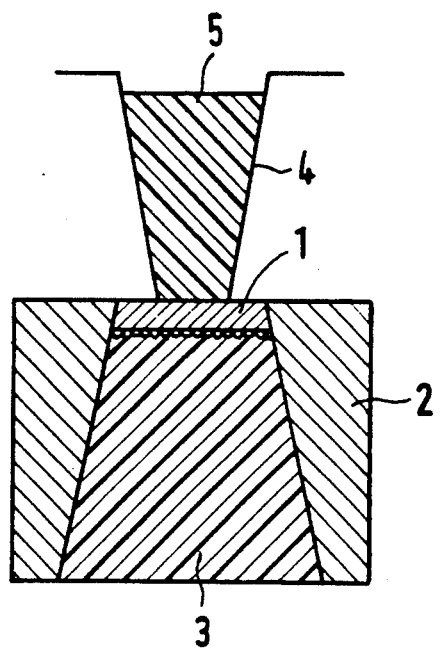
FIG. 1 shows the apparatus used for preparing samples to be tested for tensile strength.

"Particle size" as used herein refers to the primary particle size.

The hardness of the substrate and of component (A) can be determined according to the methods of Mohs, Brinell, Knoop or Vickers. The same method should be used for testing the hardness of the substrate and component (A). For testing the hardness of very fine material (e.g., less than 1 μm) the same material is used in coarser form.

The use of a sand blasting composition containing component (A) of the invention having a hardness exceeding that of the substrate results in at least a 30%, and preferably a 50% increase in bond strength as compared to sand blasting with a composition without component (A).

The substrate surfaces prepared according to the invention can be adhered, coated, or faced with commercially available adhesives, coating or facing compositions. In this way materials such as wood, metal, ceramic, synthetic resin or glass surfaces can be bonded to other wood, metal, glass, ceramic or synthetic resin surfaces.

The method of the invention offers at least the following five (5) advantages:

1) The method of the present invention does not require a sputtering apparatus, a flame hydrolysis burner, or a ceramic furnace for applying a siliceous coupling layer. The present method only requires a readily available sand blasting apparatus.

2) The method of the invention utilizes commercially available precious and non-precious metals and alloys thereof.

3) The method of the invention does not require high temperatures. The lower operating temperatures of the present invention minimize the risk that the metallic work will warp.

4) It is a particular advantage of the method of the invention that it can also be used for repairing work on damaged parts in situ (e.g., repairing of crowns and bridges with metal structures already installed in the mouth). This is hardly possible with the above-described prior art methods.

5) A special advantage of the method of the invention resides in the fact that the substrate-synthetic resin bond produced after the pre-treatment of the substrate surface according to the invention exhibits excellent hydrolytic stability. The adhesive bond has high storage stability even after storage in water or in the mouth for an extended period of time.

In the method of the invention materials such as wood, metal, ceramic, glass, or synthetic resin surfaces can be used as the substrate surface. Preferably, metallic surfaces are used.

The material of component (A) comprises 0.01 to 90% by weight, based on the total weight of the sand blasting composition, of an optionally silanized material having a particle size less than 5 μm and having a hardness exceeding that of the substrate surface. Preferably, component (A) comprises 0.1 to 30% by weight, and is more preferably composed of a material having a particle size less than 1 μm. Material of component (A) having a particle size less than 0.1 μm is especially preferred.

In a preferred embodiment, the material used as component (A) is silanized.

A siliceous material is preferably used as component (A), particularly 0.01 to 50% by weight of optionally silanized siliceous material.

Especially preferred materials for component (A) include the following: quartz, quartz glass, silicate glass containing at least 10% by weight of silicon, silicon carbide, silicon nitride and/or pyrogenic silicic acid; alumina, titania and/or zirconia as well as oxides, nitrides and/or carbides of the 3rd and 4th main group and the auxiliary group 4b. This material may have, for example, an average particle size of 10 μm; however, it must still contain at least 0.01% by weight of an optionally silanized material having a particle size less than 5 μm.

A particularly preferred material is pyrogenic silicic acid having an average particle size in the range of about 0.001 to 0.05 μm.

Component (A) must be inert under the reaction conditions. The preferred materials for component (A) are also inert at impact temperatures greater than 1000° C.

The sand blasting composition preferably comprises component (B) in an amount of 20 to 100% by weight, based on the total weight of the sand blasting composition, of a silanized siliceous material having an average particle size of 2 to 200 μm. More preferably, component (B) comprises 50 to 100% by weight of a preferred material having an average particle size of 5 to 100 μm. The silanized siliceous material may comprise, for example, quartz, quartz glass, silicate glass containing at least 10% by weight of silicon, silicon nitride, silicon carbide, or ceramic material containing at least 10% by weight of silicon. Especially preferred materials are quartz glass, silicate glass, and amorphous silicon nitride. When silicate glasses and siliceous ceramic materials are used, materials having a silicon content greater than 30% by weight are preferred.

The sand blasting composition having an average particle size greater than 5 μm to be used according to the invention as component (C) is, for example, aluminum oxide (corundum). The average particle size for component (C) is preferably greater than 5 to 500 μm, especially 20 to 250 μm. On the other hand, quartz, quartz glass, silicates, silicate glasses, silicon nitride, silicon carbide, or silicon-containing ceramic material may be advantageously employed.

As components (A) and/or (B) and (C), preferably a material of equal composition but differing particle sizes is used.

If components of the sand blasting composition are silanized, they preferably contain 0.1 to 20 % by weight of silane, particularly to 5% by weight, based on the weight of the component in the sand blasting composition. Silanizing is effected in a manner known per se, as practiced, for example, in the filler technology. All of the customarily employed silanes are suited for the preparation of the components of the sand blasting composition used according to the invention. Especially suited silanes are vinyl trimethoxysilane, γ-glycidoxypropyl trimethoxysilane, γ-methacroyloxy propyltrimethoxysilane and tetramethyl divinyl silazane. The compounds are preferably employed in the form of alcoholic or aqueous acid (e.g., acetic acid) solution.

Silanizing of the applied siliceous coupling layer is effected in a manner known per se. Preferably employed silanes are vinyl trimethoxysilane, γ-glycidoxypropyl trimethoxysilane, γ-methacroyloxy propyltrimethoxysilane and tetramethyl divinyl silazane. The compounds are preferably employed in the form of alcoholic or aqueous acid (e.g., acetic acid) solution.

It has proved to be particularly advantageous, both for the silanizing components of the sand blasting agent and also for the silanizing of the metal surface treated according to the invention, to use silanes having the same functional groups as those contained in the monomer of the synthetic resin (e.g., of the adhesive). Thus, for example, in order to adhere metals to epoxy resins, silanes having epoxy end groups are advantageously used.

The following examples of the invention will further describe and explain the features and advantages of the invention. The examples demonstrate by model experiments that the method of the invention results in surprisingly high adhesive strength and durability of the bond between metal and synthetic resin.

(A) EXAMPLES OF SYNTHETIC RESIN COATS ON DENTAL METAL ALLOYS

MEASURING METHODS

In order to examine the adhesive strength of a synthetic resin to metal, the following tensile test is carried out (see FIG. 1).

Round disks (1) of the metals to be tested having a 12 mm diameter and a 2 mm thickness are cast. The back side is provided with retention beads. The area to be tested is blasted with 250 μm alumina for 5 seconds for cleaning.

After the surface treatment, an opacifier on the basis of methacrylate (Dentacolor-Opaker, Messrs. Kulzer) is applied. After the latter has cured (e.g., 90 seconds in the Dentacolor XS apparatus, Messrs. Kulzer) the test disk (1) is fixed in the holder (2) by a self-hardening casting resin (Vitron, Messrs. ESPE) (3). A round, upwardly conically flaring metal cap (4) (diameter 7 mm at the adhesive surface) is placed thereon and filled layer-wise with photocuring facing material (5) (Visio ®-Gem, Messrs. ESPE), and cured.

The thus prepared samples are stored for 20 hours at 36° C. in water, then exposed for 6 hours in a bath of changing temperature (15° to 70° C.) with 1 minute turns. Thereafter, the samples are mounted in a universal tester (Messrs. Zwick, Model 1435) and pulled apart at a rate of 1 mm/min. The tearing force was measured and on the basis thereof the adhesive strength is calculated in MPa. In each test five test disks are used, and the average is formed therefrom.

COMPARATIVE EXAMPLES 1 TO 4

Adhesion to Precious Metal Alloy: Degulor M, Messrs, Degussa

| No. | Method | After-Treatment (Silanizing) | Adhesive Strength (MPa) (average of 5 Samples) |
|---|---|---|---|
| 1 | mechanical retention beads, 0.6 mm diameter | — | 8.8 |
| 2 | sand blasting[1] with Al$_2$O$_3$ (average particle size about 250 μm) | — | 2.9 |
| 3 | sand blasting[1] with Al$_2$O$_3$ average particle size about 250 μm | silanizing solution (A)[2] | 3.7 |
| 4 | sand blasting[1] with non-silanized quartz (average particle size about 25 μm; portion of particle size less than 5 μm, less than 0.01% by weight) | silanizing solution (A)[2] | 2.5 |

[1]time: 10 seconds; pressure: 4 bar; sand blasting apparatus FG 3-82 Sandmaster, Messrs. Unitol AG/Ltd., CH-4663 Aarburg.
[2]Silanizing Solution A = freshly prepared solution of 1 part γ-methacroyloxypropyl-trimethoxysilane and 15 parts of a solution of 87% ethanol, 3% acetic acid, and 10% water.

Comparative Example 1 describes the provision of mechanical retention by retention beads, which is a conventional prior art method. This method does not produce a chemical bond between the metal and the synthetic resin, but rather, it effects a purely mechanical anchoring which has proved to offer good adhesion results. However, such mechanical anchoring leads to marginal gaps between the synthetic resin material and the metal due to the lack of a chemical bond, and it also effects increased application of metal, which influences the color to be achieved by the synthetic resin facing.

Comparative Example 2 describes an experiment where the material is merely sand blasted with commercially available corundum.

Comparative Example 3 corresponds to Example 2, with the only exception that the treated surface is thereafter silanized.

Comparative Example 4 corresponds to Example 3, with the exception that quartz having an average particle size of 25 μm is used as the blasting agent.

DISCUSSION OF COMPARATIVE EXAMPLES 1 TO 4

Satisfactory bond strength is achievable exclusively with mechanical retention (e.g., from clinical tests it is known that adhesion values greater than 6.7 MPa withstand normal chewing stress in the mouth; cf. for example M. Rimpler, R. Hallbach-Moritz, G. Geibel and M. Pepping; Deutsche zahnarztliche Zeitung, Vol. 37, pages 321 to 324, 1982). Mere sand blasting with non-silanized alumina or quartz does not provide satisfactory adhesion results, not even upon after-treatment with silanizing solutions.

EXAMPLES 5 TO 11 (SILANIZED BLASTING AGENTS)

Sample disks made from Degulor M (Messrs. Degussa) are blasted for 30 seconds with the $SiO_2$-containing blasting agent at 4 bar (sand blaster FG-32 Sandmaster).

| No. | Blasting Medium | After-Treatment (Silanizing) | Adhesion (MPa) (Average of 5 Samples) |
|---|---|---|---|
| 5 | quartz 25 $\mu m^{(4)}$ 1% sil.[1] | silanizing solution A | 10.5 (invention) |
| 6 | quartz 25 $\mu m^{(4)}$ 1% sil.[1] | silanizing solution B[2] | 14.4 (invention) |
| 7 | quartz 25 $\mu m^{(4)}$ 3% sil.[1] | silanizing solution A | 10.2 (invention) |
| 8 | Duran ® glass[3] about 70% $SiO_2$ 1% sil.[1] | silanizing solution A | 8.9 (invention) |
| 9 | Duran[R] glass[3] 3% sil.[1] | silanizing solution A | 11.3 (invention) |
| 10 | $Al_2O_3$ 110 $\mu m^{(4)}$ 3 sil.[1] | silanizing solution A | 4.26 (comparison) |
| 11 | $Al_2O_3$ 26 $\mu m^{(4)}$ 3% sil.[1] | silanizing solution A | 4.27 (comparison) |

[1] according to conventional silanizing method with γ-methacroyloxypropyl-trimethoxysilane
[2] like silanizing solution A, but divinyl tetramethyl disilizane in lieu of γ-methacroyloxypropyl-tri-methoxysilane
[3] Messrs. Schott, medium particle size about 20 $\mu m$
[4] medium particle size (3) Messrs. Schott, medium particle size about 20 $\mu m$
(4) medium particle size

DISCUSSIONS OF EXAMPLES 5 TO 11

Examples 5 to 11 show that adequate bond strength is achieved only if the silanized homogeneous blasting agent contains a sufficient amount of silica. In Tests 5 to 9 (invention), the rupture invariably occurs in the synthetic resin layer (e.g., adhesion greater than cohesion).

EXAMPLES 12 AND 13 (NON-SILANIZED BLASTING AGENT CONTAINING PYROGENIC SILICIC ACID)

Test Disks: Degulor M, Messrs. Degussa
Blasting Agent: $Al_2O_3$, medium particle size, about 250 $\mu m$, containing pyrogenic silicic acid of average particle size of about 0.04 $\mu m$ (Aerosil ®OX50 Degussa)
Blasting Period: 10 sec. (5 bar)
After-Treatment: Silanizing Solution A

| No. | Proportion of Pyrogenic Silicic Acid (% by Wt.) | Adhesive Strength (MPa) (Average of 5 Samples) |
|---|---|---|
| 12 | 5 | 12.8 |
| 13 | 20 | 11.8 |

DISCUSSION OF EXAMPLES 12 AND 13

The tests demonstrate that minor proportions of non-silanized pyrogenic silicic acid to a commercial sand blasting agent and silanizing after-treatment provide good adhesion results between synthetic resin and metal.

The material tore in each instance within the synthetic resin layer, and thus, the adhesion of the bond is greater than the cohesion of the synthetic resin.

EXAMPLES 14 TO 18 (VARIOUS METALS)

Sand Blasting $Al_2O_3$ of medium particle size
Composition: about 250 $\mu m$, containing 5% by weight of pyrogenic silicic acid of medium particle size of about 0.04 $\mu m$ (Aerosil (R) OX50)
Degree of Silanization of the Silicic Acid: 3%
Blasting Period: 10 sec. at 5 bar
After-Treatment: Silanizing Solution A

| No. | Metal Employed | Adhesive Strength (MPa) (average of 5 samples) |
|---|---|---|
| 14 | Degulor M[1] | 12.8 |
| 15 | Stabilor G[2] | 12.8 |
| 16 | Wiron 88[3] | 13.2 |
| 17 | Wironit[4] | 16.7 |
| 18 | Palliag[5] | 10.1 |

[1] highly concentrated gold alloy, Messrs. Degussa
[2] precious metal depleted alloy, Messrs. Degussa
[3] chromium—nickel alloy, Messrs. Bego
[4] chromium—cobalt alloy, Messrs. Bego
[5] palladium—silver alloy, Messrs. Degussa

DISCUSSION OF EXAMPLES 14 TO 18

The results impressively demonstrate that with the method of the present invention all the metals commercially used in the dental area ranging from highly concentrated gold alloy to non-precious metal alloys may be employed

EXAMPLES 19 TO 21 (SAND BLASTING AGENTS USED ACCORDING TO THE INVENTION WITHOUT SILANIZING AFTER-TREATMENT)

Test Disks: Degulor M, Messrs. Degussa
Blasting Period: 10 sec. (5 bar)
After-Treatment: none

| No. | Pyrogenic Silicic Acid of average Particle Size of about 0.04 $\mu m$ (Wt. %) | Blasting Agent $Al_2O_3$ of average Particle Size | Adhesive Strength (MPa) (Average of 5 Samples) |
|---|---|---|---|
| 19 | 5% 3% sil. | about 250 $\mu m$ | 8.2 |
| 20 | 5% non-sil. | about 250 $\mu m$ | 11.1 |
| 21 | 1% non-sil. | about 110 $\mu m$ | 10.9 |

DISCUSSION OF EXAMPLES 19 TO 21

The tests also show that without silanizing after-treatment, good adhesion between the synthetic resin and the metal is obtained.

EXAMPLES 22 TO 25 WITH VARIOUS ADDITIVES

Test disks: Degulor M
Blasting Agent $Al_2O_3$, average particle size about 250 $\mu m$, + additive
Blasting Period 10 sec. at 5 bar
After-Treatment Silanizing solution A

| Additive | Adhesive Strength (MPa) (average |

-continued

| No. | (% by wt) | of 5 Samples) |
|---|---|---|
| 22 | 5% pyrogenic silicic acid of average particle size of about 0.008 μm (Aerosil 380, Degussa) (non-silanized) | 9.1 |
| 23 | 5% pyrogenic silicic acid of average particle size of about 0.008 μm (Aerosil 380, Degussa) (3% silanized)[1] | 8.6 |
| 24 | 5% glass powder of average particle size of 2 μm containing 25% by wt of portions of particle size less than 1 μm (GM X087, Messrs. Schott Landshut) (3% silanized)[1] | 8.5 |
| 25 | 5% silicon nitride, contains 60% by wt of portions less than 1 μm (Messrs. Toyo Soda, Japan) | 12.3 |

[1] with γ-methacryloxypropyl trimethoxysilane

DISCUSSION OF EXAMPLES 22 TO 25

The tests demonstrate that good adhesion results are obtained if sufficient silicon-containing material less than μm is contained in the sand blasting medium.

(B) EXAMPLES FOR METAL-TO-METAL ADHESION

MEASURING METHOD

Figure 2:
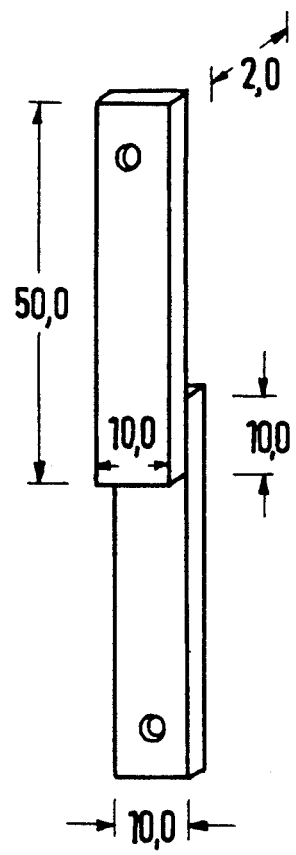
FIG. 2 shows the relationship between the molded parts of metal to be tested to determine adhesive strength.

The adhesive strength of the bond is determined by means of a tensile/shear test. Molded parts of the metal to be tested are adhered in an overlapping relationship (e.g., adhered surface 1 cm$^2$), as illustrated by FIG. 2.

The adhered samples are exposed for 6 hours to a changing temperature bath (15° to 70° C.) with one-minute intervals of change. Thereafter, the tear-off force is measured by means of a universal tester (Messrs. Zwick, model 1435) at a rate of advance of 1 mm/min, and the adhesive strength in MPa is calculated therefrom. For each test, 5 bonds are made and the mean value is calculated therefrom.

EXAMPLE 26

1. A surface is cleaned by sand-blasting for 10 seconds with Al$_2$O$_3$ (110 μm average particle size).
2. Sand-blasting occurs for 10 seconds with Al$_2$O$_3$ (110 μm average particle size) containing 1% pyrogenic silicic acid having an average particle size of about 0.04 μm (Aerosil OX 50) non-silanized at 2.5 bar blasting pressure.
3. A freshly prepared silanizing solution is applied which comprises 1 part of γ-glycidoxypropyl-trimethoxysilane and 15 parts of a solution of 87% ethanol, 3% acetic acid, and 10% water.
4. After the surface treatment is terminated (e.g., steps 1 to 3 above), a 2-component epoxy adhesive (UHU (R) hard) is bonded at a ratio of 1:1. Both areas to be adhered are coated, fixed under 3 kp pressure, and cured for 20 hours at room temperature. Thereafter, a 10 minute after-curing period at 180° C. followed.

EXAMPLE 27 (COMPARISON WITHOUT SURFACE COATING)

Adhesion as in Example 26, except that the pretreatment merely comprises step 1 (e.g., 10 seconds blasting with Al$_2$O$_3$). Thus, steps 2 and 3 are omitted.

EXAMPLE 28

Adhesion as described in Example 26, but with the following modifications:
Step 3: γ-methacroyloxypropyl trimethoxysilane is used instead of γ-glycidoxypropyl trimethoxysilane;
Step 4: After performance of the surface treatment there follows adhesion with a 2-component adhesive based on acrylate (Nimetic ®-Grip, Messrs. ESPE). The two components are blended at a ratio of 1:1, applied on both surfaces to be adhered, fixed at 30 N pressure, and cured for 20 hours at 23° C.

EXAMPLE 29 (COMPARISON WITHOUT SURFACE COATING)

Adhesion as in Example 28, except that the pretreatment merely comprises step 1 (e.g., 2 and 3 are omitted).

MEASURING RESULTS

| Example | Adhesive | Tensile Shear Strength (MPa) |
|---|---|---|
| 26 (invention) | epoxy resin | 28.6 |
| 27 (comparison) | epoxy resin | 13.6 |
| 28 (invention) | acrylate | 18.4 |
| 29 (comparison) | acrylate | 13.0 |

DISCUSSION OF EXAMPLES 26 TO 29

In making metal-to-metal bonds the method of the invention results in distinctly higher tensile shear strength than by merely sand blasting the surface with Al$_2$O$_3$. The tests favorably demonstrate that in the method of the invention the silanizing step 3 with silanes is performed wherein the functional groups of which permit copolymerization with the adhesive employed. Thus, for adhesion with epoxy adhesives, suitably epoxy-functional silanes can be employed; and for adhesion with acrylate type adhesives, acrylate or methacrylate functional silanes can be selected.

EXAMPLES 30 TO 33 WITH VARIOUS ADDITIVES

Test disks: Degulor M, Mohs hardness 6
Blasting Agent: Al$_2$O$_3$, average particle size about 250 μm, +additive
Blasting Period: 10 sec. at 5 bar
After-Treatment: Silanizing Solution A

| | Test disks: | Degulor M, Mohs hardness 6 | |
|---|---|---|---|
| | Blasting Agent: | Al$_2$O$_3$, average particle size about 250 μm, + additive | |
| | Blasting Period: | 10 sec. at 5 bar | |
| | After-Treatment: | Silanizing solution A | |

| No. | Addition (% by Wt) | Mohs Hardness | Adhesive Strength (MPa) (average from 5 samples) |
|---|---|---|---|
| 30 (invention) | 2% zirconia (pyrogenic, average particle size about 0.04 μm) | 8 | 12.4 |
| 31 (invention) | 2% alumina (average particle size 0.04–0.2 μm) | 9 | 18.3 |
| 32 (invention) | 3% titania (P 25, pyrogenic, Messrs. Degussa average particle size 0.03 μm) | 6–7 | 12.8 |
| 33 (compara- | 3% calcium fluoride, precipitated (Messrs. | 4 | 5 |

| (tive test) | Merck average particle size about 0.3 μm) |
|---|---|

RESULTS:

The results demonstrate that good adhesive values are attained in all cases where the hardness of the additive used according to the invention is greater than that of the blasting medium, Degulor M having a hardness of 6, and where the particle size is sufficiently small. In each one of the described test set-ups, the test body, after performance of the adhesive strength measurements, tore in the synthetic resin (e.g., in the Opaker material).

In the comparative test, no traces of synthetic resin (e.g., Opaker) are left on the torn-off metal disk. The tear extends exclusively along the substrate/synthetic resin interface.

EXAMPLES 34 TO 37, ADHESION OF SYNTHETIC RESIN/SYNTHETIC RESIN BONDS

The test set-up is analogous to that of Examples 5 to 11, except that the substrates employed are confectioned synthetic resin teeth on crosslinked PMMA basis (Biodent, Messrs. DeTrey/Dentsply), rather than cast metal disks. The adhering faces of the synthetic resin teeth are ground even and (in contrast to Examples 5 to 11) are sand blasted for 5 seconds with alumina having a particle size less than 110 μm for cleaning purposes.

The treatment according to the invention is performed with alumina having a particle size less than 110 μm plus the quantities of the additive according to the invention stated in the Table below. Thereafter, the surface area is coated with silanizing solution B, the round metal cap (4) opening conically towards the top is put in place and is directly filled in layers with the photocuring facing material (5) (Visio®-Gem, Messrs. ESPE) and then cured.

| No. | Blasting Material Additive (% by Wt) | Mohs Hardness | Mohs Hardness of Substrate (Biodent Tooth) | Adhesive Strength (MPa) |
|---|---|---|---|---|
| 34 (invention) | 2% by wt of SnO$_2$ (average particle size about 0.8 μm) | 6–7 | 3 | 11 |
| 35 (invention) | 2% by wt of calcium fluoride (Merck, average particle size about 0.3 μm) | 4 | 3 | 12.5 |
| 36 (invention) | 1% by wt of pyrogenic silicic acid of average particle size of about 0.4 μm | 6–7 | 3 | 11.5 |
| 37 (comparison) | — | — | 3 | 3.5 |

RESULTS

After pretreatment of the synthetic resin surfaces according to the invention, the adhesion strength increase to values that are 3 to 4 times higher than the comparison.

EXAMPLES 38 TO 39, CERAMIC/SYNTHETIC RESIN BOND

The test set-up corresponds to that of Examples 34 to 37, except that test disks made of dental ceramic (VMK-ceramic, Messrs, Vita) are used.

| No. | Additive to Blasting Grit (% by Wt) | Mohs Hardness | Mohs Hardness of Substrate (Biodent Tooth) | Adhesive Strength (MPa) |
|---|---|---|---|---|
| 38 (invention) | 1% by wt of pyrogenic silicic acid of average particle size of about 0.04 μm | 6–7 | 6 | 13.5 |
| 39 (comparison) | — | — | 6 | 7.5 |

RESULTS

An increase of adhesive strength by about 50% can be achieved with the additive according to the invention. Moreover, with the additive proposed with the present invention, the torn parts show a purely cohesive fracture, while in the comparative test about 50% of the fracture area is a purely adhesive fracture.

EXAMPLES 40 TO 43

In order to adhere two synthetic resin pieces of polypropylene and teflon to one another, test pieces (25 mm length, 5 mm width, 2 mm thickness) are produced from polypropylene and teflon, and two each of said test pieces are subjected to the surface treatments. Thereafter, the test pieces are coated with solution C, which is a freshly prepared solution of 1 part γ-glycidoxypropyl-trimethoxysilane and 15 parts of a solution of 87% ethanol, 3% acetic acid, and 10% water, then blown-dried, and glued together over half of their length by a two-component epoxy resin (E 32, Messrs. Delo). Prior to gluing, the surfaces are preliminarily sand-blasted with alumina having a particle size of 110 μm for 10 seconds at a pressure of 2 bar. Half of the samples are thereafter sand blasted according to the invention with an addition of 1% by weight of pyrogenic silicic acid of medium particle size of about 0.04 μm (OX 50, Messrs. Degussa) to the alumina for a period of 10 seconds. The results are compiled in the Table below.

| No. | Additive to Blasting Grit | Substrate | Adhesive Strength (MPa) |
|---|---|---|---|
| 40 (invention) | 1% by wt of pyrogenic silicic acid of average particle size of about 0.04 μm | polypropylene | 4 |
| 41 (comparison) | — | polypropylene | 1.5 |
| 42 (invention) | 1% by wt of pyrogenic silicic acid of average particle size of about 0.04 μm | Teflon | 3 |
| 43 (comparison) | — | Teflon | 1 |

RESULTS

With the surface treatment according to the invention, an adhesion is achievable that is two times to three times as high as that of the comparative examples.

Further scope of applicability of the present invention will become apparent from the detailed description given hereinabove. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A method for preparing a substrate surface for bonding with a synthetic resin which comprises:
    applying a coupling layer on said substrate by sand blasting with a composition which, based on the weight of the entire sand blasting composition, comprises:
    (A) 0.01 to 90% by weight of an optionally silanized material having a particle size less than 5 μm and having a hardness exceeding that of the substrate surface, or
    (B) 20 to 100% by weight of a silanized siliceous material having an average particle size of about 2 to 200 μm, wherein
    (C) any remainder of the sand blasting composition, if present, has an average particle size greater than 5 μm, and thereafter, optionally silanizing said coupling layer.

2. The method according to claim 1, wherein the substrate surface is a metallic surface.

3. The method according to claim 1, wherein said composition comprises component (A) in an amount of about 0.01 to 50% by weight of an optionally silanized siliceous material.

4. The method according to claim 1, wherein component (A) comprises at least one member selected from the group consisting of quartz, quartz glass, silicate glass containing at least 10% by weight of silicon, pyrogenic silicic acid, silicon carbide and silicon nitride.

5. The method according to claim wherein component (A) comprises at least one member selected from the group consisting of alumina, titania, and zirconia.

6. The method according to claim 1, wherein component (A) has a particle size less than 1 μm.

7. The method according to claim 6, wherein component (A) has a particle size less than 0.1 μm.

8. The method according to claim 1, wherein component (A) comprises pyrogenic silicic acid having an average particle size in a range of about 0.001 to 0.05 μm.

9. The method according to claim 1, wherein said composition comprises about 0.1 to 30% by weight of component (A).

10. The method according to claim 1, wherein component (B) comprises at least one member selected from the group consisting of silanized quartz, silanized quartz glass, silanized silicate glass containing at least 10% by weight of silicon, silanized ceramic material containing at least 10% by weight of silicon, silanized silicon nitride and silanized silicon carbide.

11. The method according to claim 10, wherein component (B) has an average particle size in a range of greater than 5 up to 100 μm.

12. The method according to claim 10 wherein said composition comprises about 50 to 100% by weight of component (B).

13. The method according to claim 1, wherein the substrate surface is selected from the group consisting of wood, metal, ceramic, glass and synthetic resin surfaces.

14. The method according to claim 1, wherein the material of component (A) is silanized.

15. The method according to claim wherein component (B) comprises at least one member from the group consisting of quartz glass, silicate glass and amorphous silicon nitride.

16. The method according to claim 1, wherein component (B) comprises silicate glass or siliceous ceramic materials having a silicon content greater than 30% by weight.

17. The method according to claim 1, wherein component (C) is aluminum oxide.

18. The method according to claim wherein the average particle size of component (C) is about 5 to 500 μm.

19. The method according to claim 1, wherein the sand blasting composition comprises about 0.1 to 20% by weight silane.

20. A method for bonding a synthetic resin to a substrate surface, which comprises:
    applying a coupling layer on said substrate surface by sand blasting with a composition which, based on the weight of the entire sand blasting composition, comprises:
    (A) 0.01 to 90% by weight of an optionally silanized material having a particle size less than 5 μm and having a hardness exceeding that of said substrate surface and/or
    (B) 20 to 100% by weight of a silanized siliceous material having an average particle size of 2 to 200 μm, and wherein
    (C) any remainder of the sand blasting composition if present, has an average particle size greater than 5 μm, and thereafter, optionally silanizing said coupling layer, and
    bonding said synthetic resin to said substrate surface.

21. The method according to claim 1, which further comprises applying an adhesive layer to said substrate surface after sand blasting.

22. The method of claim 1 wherein the sand blasting composition comprises (A) and (C), or (B) and (C), or (A), (B) and (C).

23. The method of claim 20 wherein the sand blasting composition comprises (A) and (C), or (B) and (C), or (A), (B) and (C).

* * * * *

UNITED STATES PATENT AND TRADEMARK OFFICE
CERTIFICATE OF CORRECTION

PATENT NO. : 5,024,711

DATED : June 18, 1991

INVENTOR(S) : GASSER et al.

It is certified that error appears in the above-identified patent and that said Letters Patent is hereby corrected as shown below:

Column 13, line 44:
Claim 5, Line 1, change "claim" to --claim 1--.
Column 14, line 17:
Claim 15, Line 1, change "claim" to --claim 1--.
Column 14, line 28:
Claim 18, Line 1, change "claim" to --claim 1--.

Signed and Sealed this

Fifth Day of January, 1993

Attest:

DOUGLAS B. COMER

Attesting Officer

Acting Commissioner of Patents and Trademarks